US009795568B2

(12) United States Patent
Folger et al.

(10) Patent No.: US 9,795,568 B2
(45) Date of Patent: *Oct. 24, 2017

(54) LOW CONCENTRATION MELOXICAM TABLETS

(75) Inventors: Martin A. Folger, Ingelheim am Rhein (DE); Stefan Lehner, Wiesbaden (DE); Horst Schmitt, Nieder-Hilbersheim (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 200 days.

This patent is subject to a terminal disclaimer.

(21) Appl. No.: 13/093,886

(22) Filed: Apr. 26, 2011

(65) Prior Publication Data

US 2011/0275618 A1    Nov. 10, 2011

(30) Foreign Application Priority Data

May 5, 2010   (EP) .................................... 10162015

(51) Int. Cl.
*A61K 31/5415* (2006.01)
*B29C 43/02* (2006.01)
*A61K 9/20* (2006.01)
*A61K 9/00* (2006.01)

(52) U.S. Cl.
CPC .......... *A61K 9/2072* (2013.01); *A61K 9/0056* (2013.01); *A61K 9/2095* (2013.01); *A61K 31/5415* (2013.01)

(58) Field of Classification Search
None
See application file for complete search history.

(56) References Cited

U.S. PATENT DOCUMENTS

| | | |
|---|---|---|
| 2,795,529 A | 6/1957 | Alburn et al. |
| 3,288,675 A | 11/1966 | Newmark et al. |
| 3,849,549 A | 11/1974 | Dempski et al. |
| 3,931,212 A | 1/1976 | Satzinger et al. |
| 3,947,576 A | 3/1976 | Kuczkowski et al. |
| 4,233,299 A | 11/1980 | Trummlitz et al. |
| 4,482,554 A | 11/1984 | Gebhardt et al. |
| 4,628,053 A | 12/1986 | Fries |
| 4,687,662 A | 8/1987 | Schobel |
| 4,702,919 A | 10/1987 | Kitamori et al. |
| 4,748,174 A | 5/1988 | Veronesi |
| 4,794,117 A | 12/1988 | Corbiere |
| 4,835,187 A | 5/1989 | Reuter et al. |
| 4,942,167 A | 7/1990 | Chiesi et al. |
| 5,026,560 A | 6/1991 | Makino et al. |
| 5,169,847 A | 12/1992 | Nagy et al. |
| 5,283,065 A | 2/1994 | Doyon et al. |
| 5,304,561 A | 4/1994 | Sarfarazi |
| 5,360,611 A | 11/1994 | Robertson et al. |
| 5,414,011 A | 5/1995 | Fu et al. |
| 5,654,003 A | 8/1997 | Fuisz et al. |
| 5,700,816 A | 12/1997 | Isakson et al. |
| 5,811,446 A | 9/1998 | Thomas |
| 5,824,658 A | 10/1998 | Falk et al. |
| 5,886,030 A | 3/1999 | Maniar |
| 6,046,191 A | 4/2000 | Hamley et al. |
| 6,048,557 A | 4/2000 | Van Den Burg et al. |
| 6,071,539 A | 6/2000 | Robinson et al. |
| 6,106,862 A | 8/2000 | Chen et al. |
| 6,136,804 A | 10/2000 | Nichtberger |
| 6,166,012 A | 12/2000 | Muller et al. |
| 6,180,136 B1 | 1/2001 | Larson et al. |
| 6,183,779 B1 | 2/2001 | Ouali et al. |
| 6,184,220 B1 | 2/2001 | Turck et al. |
| 6,187,800 B1 | 2/2001 | Suri et al. |
| 6,221,377 B1 | 4/2001 | Meyer |
| 6,284,269 B1 | 9/2001 | Struengmann et al. |
| 6,319,519 B2 | 11/2001 | Woolfe et al. |
| 6,495,603 B1 | 12/2002 | Miyake et al. |
| 6,550,955 B2 | 4/2003 | D'Silva |
| 6,599,529 B1 | 7/2003 | Skinhøj et al. |
| 6,605,295 B1 | 8/2003 | Bellmann et al. |
| 6,630,056 B1 | 10/2003 | Thibierge et al. |
| 6,669,957 B1 | 12/2003 | Laruelle et al. |
| 6,682,747 B1 | 1/2004 | Turck et al. |
| 6,869,948 B1 | 3/2005 | Bock et al. |
| 6,986,346 B2 | 1/2006 | Hochrainer et al. |
| 7,105,512 B2 | 9/2006 | Morizono et al. |
| 7,969,206 B2 | 6/2011 | Ito |

(Continued)

FOREIGN PATENT DOCUMENTS

| | | |
|---|---|---|
| AU | 673675 B2 | 11/1996 |
| CA | 1102802 | 6/1981 |

(Continued)

OTHER PUBLICATIONS

Bi et al. (Drug Development and Industrial Pharmacy, 25(5) 571-581 (1999).*
Sharma (AAPS0 PharmSciTech 2005; 6 (4) Article 76).*
Swamy (Indian J Pharm Sci [serial online] 2007, 69: 836-40 (available online at web address www.ijpsonline.com/text.asp?2007/69/6/836/39448)).*
Techceuticals article, posted 2009, see web address //techceuticals.com/blog/?tag=particle-size.*
European Search Report for EP10162015 dated Aug. 30, 2010.

(Continued)

*Primary Examiner* — Kortney L Klinkel
*Assistant Examiner* — William Lee
(74) *Attorney, Agent, or Firm* — Marc Began; Joyce L. Morrison

(57) ABSTRACT

The invention relates to a solid tablet that is directly-compressed of powder, comprising meloxicam and one or more excipients which are homogenously dispersed within the tablet that can be broken into two, three or four units with each unit containing equal amounts of the active ingredient, meloxicam.

19 Claims, 2 Drawing Sheets

(56) References Cited

U.S. PATENT DOCUMENTS

| | | |
|---|---|---|
| 2001/0055569 A1 | 12/2001 | Davis et al. |
| 2002/0006440 A1 | 1/2002 | Cherukuri |
| 2002/0016342 A1 | 2/2002 | Scolnick et al. |
| 2002/0035107 A1 | 3/2002 | Henke et al. |
| 2002/0068088 A1 | 6/2002 | Gruber |
| 2002/0077328 A1 | 6/2002 | Hassan et al. |
| 2002/0099049 A1 | 7/2002 | Burch et al. |
| 2002/0106345 A1 | 8/2002 | Uhrich et al. |
| 2002/0131998 A1 | 9/2002 | Martani |
| 2002/0169212 A1 | 11/2002 | Stroble et al. |
| 2002/0187187 A1 | 12/2002 | Ohki et al. |
| 2003/0050305 A1 | 3/2003 | Tejada |
| 2003/0055051 A1 | 3/2003 | Morizono et al. |
| 2003/0109701 A1 | 6/2003 | Coppi et al. |
| 2003/0119825 A1 | 6/2003 | Folger et al. |
| 2003/0199482 A1 | 10/2003 | Seibert et al. |
| 2003/0220306 A1 | 11/2003 | Simmons et al. |
| 2004/0001883 A1 | 1/2004 | Matsui et al. |
| 2004/0024041 A1 | 2/2004 | Selzer |
| 2004/0024042 A1 | 2/2004 | Breyer |
| 2004/0037869 A1 | 2/2004 | Cleverly et al. |
| 2004/0043992 A1 | 3/2004 | Tolba et al. |
| 2004/0110747 A1 | 6/2004 | Altman |
| 2004/0171611 A1 | 9/2004 | Trummlitz et al. |
| 2004/0180092 A1 | 9/2004 | Henke et al. |
| 2004/0198826 A1 | 10/2004 | Baiker et al. |
| 2004/0204413 A1* | 10/2004 | Faour et al. ............... 514/248 |
| 2004/0204472 A1 | 10/2004 | Briggs et al. |
| 2004/0214753 A1 | 10/2004 | Britten et al. |
| 2004/0229038 A1 | 11/2004 | Cooper et al. |
| 2004/0234596 A1 | 11/2004 | Ohki et al. |
| 2004/0253312 A1 | 12/2004 | Sowden et al. |
| 2005/0038018 A1 | 2/2005 | Kanbe et al. |
| 2005/0147664 A1 | 7/2005 | Liversidge et al. |
| 2005/0187212 A1 | 8/2005 | Ohki et al. |
| 2005/0187213 A1 | 8/2005 | Lang et al. |
| 2005/0197332 A1 | 9/2005 | Altman |
| 2005/0244491 A1 | 11/2005 | Ohki et al. |
| 2005/0245510 A1 | 11/2005 | Friton et al. |
| 2005/0277634 A1 | 12/2005 | Janott et al. |
| 2005/0288280 A1 | 12/2005 | Friton et al. |
| 2006/0079516 A1 | 4/2006 | Henke et al. |
| 2006/0160793 A1 | 7/2006 | Altman |
| 2006/0217431 A1 | 9/2006 | Daemmgen et al. |
| 2007/0077296 A1* | 4/2007 | Folger et al. ............ 424/464 |
| 2007/0099907 A1 | 5/2007 | Altman |
| 2008/0132493 A1 | 6/2008 | Folger et al. |
| 2008/0234380 A1 | 9/2008 | Shapiro |
| 2008/0280840 A1 | 11/2008 | Lang et al. |
| 2010/0015184 A1* | 1/2010 | Tuel .......................... 424/400 |
| 2011/0083985 A1 | 4/2011 | Folger et al. |
| 2011/0275618 A1 | 11/2011 | Folger et al. |
| 2012/0077764 A1 | 3/2012 | Freehauf et al. |
| 2013/0178467 A1 | 7/2013 | Henke et al. |
| 2014/0066440 A1 | 3/2014 | Folger et al. |
| 2014/0113893 A1 | 4/2014 | Folger et al. |
| 2014/0179639 A1 | 6/2014 | Lang et al. |
| 2014/0332438 A1 | 11/2014 | Henke et al. |
| 2017/0035885 A1 | 2/2017 | Henke et al. |

FOREIGN PATENT DOCUMENTS

| | | |
|---|---|---|
| CA | 2164100 A1 | 1/1995 |
| CA | 2166204 A1 | 1/1995 |
| CA | 2326517 A1 | 10/1999 |
| CA | 2404360 A1 | 9/2001 |
| CA | 2414063 A1 | 12/2001 |
| CA | 2469588 | 6/2003 |
| CA | 2503396 A1 | 5/2004 |
| DE | 3434707 A1 | 4/1985 |
| DE | 3700172 A1 | 7/1987 |
| DE | 4217971 C1 | 10/1993 |
| DE | 19729879 A1 | 1/1999 |
| DE | 10010123 A1 | 9/2001 |
| DE | 10024752 A1 | 11/2001 |
| DE | 10032132 A1 | 1/2002 |
| DE | 10300323 A1 | 10/2004 |
| EP | 0002482 A1 | 6/1979 |
| EP | 0034432 A2 | 8/1981 |
| EP | 0093999 A2 | 11/1983 |
| EP | 0127400 A2 | 12/1984 |
| EP | 0177870 A2 | 4/1986 |
| EP | 0179430 A2 | 4/1986 |
| EP | 0306984 A1 | 3/1989 |
| EP | 0360246 A1 | 3/1990 |
| EP | 0390071 A1 | 10/1990 |
| EP | 0422681 A1 | 4/1991 |
| EP | 0465235 A1 | 1/1992 |
| EP | 0560329 A1 | 9/1993 |
| EP | 0945134 A1 | 9/1999 |
| EP | 1082966 | 3/2001 |
| EP | 1190714 A2 | 3/2002 |
| EP | 1568369 A1 | 8/2005 |
| ES | 2065846 A1 | 2/1995 |
| ES | 2159564 T3 | 10/2001 |
| FR | 2437838 A1 | 4/1980 |
| GB | 2455875 A | 6/2009 |
| IT | 1251650 B | 5/1995 |
| JP | 47007352 Y1 | 3/1972 |
| JP | S52102416 A | 8/1977 |
| JP | 1299230 A | 12/1989 |
| JP | H06157312 A | 6/1994 |
| JP | H0912426 A | 1/1997 |
| JP | 11139971 A | 5/1999 |
| JP | 2001170083 A | 6/2001 |
| JP | 2003535902 A | 12/2003 |
| JP | 3550782 B2 | 8/2004 |
| JP | 4018022 B2 | 12/2007 |
| JP | 04321624 B2 | 8/2009 |
| WO | 199301814 A1 | 2/1993 |
| WO | 1994000420 A1 | 1/1994 |
| WO | 1995009639 A1 | 4/1995 |
| WO | 1995017178 A1 | 6/1995 |
| WO | 1995018604 A1 | 7/1995 |
| WO | 1996003387 A1 | 2/1996 |
| WO | 1996003388 A1 | 2/1996 |
| WO | 1996010999 A2 | 4/1996 |
| WO | 1996011192 A1 | 4/1996 |
| WO | 1996041625 A1 | 12/1996 |
| WO | 1997003655 A1 | 2/1997 |
| WO | 1997003667 A1 | 2/1997 |
| WO | 1997017978 A1 | 5/1997 |
| WO | 1997017989 A1 | 5/1997 |
| WO | 1997029776 A1 | 8/1997 |
| WO | 1997031631 A1 | 9/1997 |
| WO | 1998017250 A1 | 4/1998 |
| WO | 1999009988 A1 | 3/1999 |
| WO | 1999012524 A1 | 3/1999 |
| WO | 1999027906 A1 | 6/1999 |
| WO | 1999039730 A1 | 8/1999 |
| WO | 1999049845 A1 | 10/1999 |
| WO | 1999049867 A1 | 10/1999 |
| WO | 1999055320 A1 | 11/1999 |
| WO | 1999059634 A1 | 11/1999 |
| WO | 2000015195 A1 | 3/2000 |
| WO | 2001008689 A1 | 2/2001 |
| WO | 2001037838 A1 | 5/2001 |
| WO | 2001052897 A2 | 7/2001 |
| WO | 2001087343 A2 | 11/2001 |
| WO | 2001097813 A2 | 12/2001 |
| WO | 2002085331 A1 | 10/2002 |
| WO | 2003049733 A2 | 6/2003 |
| WO | 2003082297 A1 | 10/2003 |
| WO | 2003097066 A1 | 11/2003 |
| WO | 2004004776 A1 | 1/2004 |
| WO | 2004026116 A2 | 4/2004 |
| WO | 2004026313 A1 | 4/2004 |
| WO | 2004037264 A1 | 5/2004 |
| WO | 2004089379 A2 | 10/2004 |
| WO | 2004103283 A2 | 12/2004 |
| WO | 2005002542 A2 | 1/2005 |
| WO | 2005004915 A2 | 1/2005 |
| WO | 2005079806 A1 | 9/2005 |
| WO | 2005105101 | 11/2005 |

(56) References Cited

FOREIGN PATENT DOCUMENTS

| WO | 2005115386 A1 | 12/2005 |
|---|---|---|
| WO | 2006000306 A1 | 1/2006 |
| WO | 2006015942 A1 | 2/2006 |
| WO | 2006100213 A1 | 9/2006 |
| WO | 2007039417 A1 | 4/2007 |
| WO | 2007135505 A2 | 11/2007 |
| WO | 2008113149 A2 | 9/2008 |
| WO | 2011046853 A1 | 4/2011 |
| WO | 2011107498 A1 | 9/2011 |
| WO | 2011138197 A2 | 11/2011 |

OTHER PUBLICATIONS

"Committee for Veterinary Medicinal Products—Meloxicam (Extension to PIGS)—Summary Report (5)". The European Agency for the Evaluation of Medicinal Products, Veterinary Medicines and Information Technology, Dec. 2000, pp. 1-3.
"Metacam (R) 0.5 mg/ml oral suspension for cats." Boehringer Ingelheim Datasheet, WEB site: http://www.vetgb.com/vetgb_pdfs/metacamc_7a5c_vetgb.pdf>Accessed on Jun. 8, 2010.
"Metacam(R)"FDA Animal & Veterinary Drug Labels, WEB site: http://www.fda.gov/downloads/AnimalVeterinary/Products/ApprovedAnimalDrugProducts/DrugLabels/UCM050397.pdf>Accessed on Jun. 8, 2010.
"Metacam—Community register of veterinary medicinal products" accessed online at http://pharmacos.eudra.org/F2/register/v004.htm.
"Types of Solutions". University of Wisconsin, Stevens Point, Feb. 1, 2001, accessed at http://www.uwsp.edu/chemistry/tzamis/chem106pdfs/solutionexamples.pdf, Google date sheet included, 2 pages.
Abstract in English of DE10024752, 2001.
Abstract in English of FR2437838, 1980.
Abstract in English of JP47007352, 1972.
Abstract in English of DE3434707, 1985.
Abstract in English of JP02906528, 1999.
Abstract in English of JP11139971, 1999.
Altman et al., "Efficacy Assessment of Meloxicam, a Preferential Cyclooxygenase-2 Inhibitor, in Acute Coronary Syndromes Without ST-Segment Elevation: The Nonsteroidal Anti-Inflammatory Drugs in Unstable Angina Treatment-2 (NUT-2) Pilot Study". Circulation, vol. 106, 2002, pp. 191-195.
Ansel et al., "Pharmaceutical Dosage Forms and Drug Delivery Systems". Seventh Edition, Lippincott Williams & Wilkins, Philadelphia, PA, 1999, pp. 77-87.
Bednarek et al., "Effect of steroidal and non-steroidal anti-imflammatory drugs in combination with long-acting oxytetracycline on non-specific immunity of calves suffering from enzootic bronchopneumonia". Veterinary Microbiology, vol. 96, 2003, pp. 53-67.
Bednarek et al., "The effect of steroidal and non-steroidal anti-inflammatory drugs on the cellular immunity of calves with experimentally-induced local lung inflammation". Veterinary Immunology and Immunopathology, vol. 71, 1999, pp. 1-15.
Boehringer Ingelheim; Metacam (Meloxicam) Now Approved for Pigs and Mastitis in Dairy Cows; May 2003 Press Release; pp. 1-2.
Cho et al., "In vitro effects of Actinobacillus pleuropneumoniae on inducible nitric oxide synthase and cyclooxygenase-2 in porcine alveolar macrophages". American Journal of Veterinary Research, vol. 64, No. 12, Dec. 2003, pp. 1514-1518.
D'Yakov et al., "Long term use of Tamsulosin (omnic®) in Patients with Chronic Prostatitis". Urologiia, vol. 5, 2002, pp. 10-12.
Del Tacca et al., "Efficacy and Tolerability of Meloxicam, a COX-2 Preferential Nonsteroidal Anti-Inflammatory Drug". Clinical Drug Investigation, vol. 22, No. 12, 2002, pp. 799-818.
Dellabella et al., "Conservative Managment of Juxtavesical Calculi with Tamsulosin". European Urology Supplements, vol. 2, No. 1, 2003, p. 81.
Dow Chemicals Brochure, entitled "Using METHOCEL cellulose ethers for controlled release of drugs in hyrophilic matrix systems." Publication Jul. 2000, Form No. 198-02075-700 AMS, pp. 1-36.

Dunn et al., "Tamsulosin: A Review of its Pharmacology and Therapeutic Efficacy in the Management of Lower Urinary Tract Symptoms". Drugs & Aging, vol. 19, No. 2, 2002, pp. 132-161.
Engelhardt et al., "Meloxicam: Influence on Arachidonic Acid Metabolism". Biochemical Pharmacology, vol. 51, 1996, pp. 21-28.
Ettmayer et al., "Lessons Learned from Marketed and Investigational Prodrugs". Journal of Medicinal Chemistry, vol. 47, No. 10, May 2004, pp. 2393-2404.
European Search Report for EP10155400 dated Jun. 9, 2010.
Farkouh et al., "Comparison of lumiracoxib with naproxen and ibuprofen in the Therapeutic Arthritis Research and Gastrointestinal Event Trial (TARGET), cardiovascular outcomes: randomised controlled trial". Lancet, vol. 364, Aug. 2004, pp. 675-684.
Fitzgerald et al., "COX-2 inhibitors and the cardiovascular system". Clinical and Experimental Rheumatology, vol. 19, No. 6, Supp. 25, Nov. 2001, pp. S31-S36.
Fitzpatrick et al., "Recognising and Controlling Pain and Inflammation in Mastitis". Proceedings of the British Mastitis Conference, Axient/Institute for Animal Health, Milk Development Council/Novartis Animal Health, 1998, pp. 36-44.
Giuliani et al., "Role of Antithrombotic Therapy in Cardiac Disease". Mayo Clinic Practice of Cardiology, Third Edition, Mosby, St. Louis, MO, 1996, pp. 1116-1121.
Gollackner et al., "Increased apoptosis of hepatocyctes in vascular occulusion after orthotopic liver transplantation". Transplant International, vol. 13, No. 1, 2000, pp. 49-53.
Gruet et al., "Bovine mastitis and intramammary drug delivery: review and perspectives". Advanced Drug Delivery Reviews, vol. 50, 2001, pp. 245-259.
Guth et al., "Pharmacokinetics and pharmacodynamics of terbogrel, a combined thromboxane A2 receptor and synthase inhibitor, in healthy subjects". British Journal of Clinical Pharmacology, vol. 58, No. 1, Jul. 2004, pp. 40-51.
Hawkey et al., "Gastrointestinal Tolerability of Meloxicam Compared to Diclofenac in Osteoarthritis Patients". British Journal of Rheumatology, vol. 37, No. 9, 1998, pp. 937-945.
Hirsch et al, "Investigation on the efficacy of meloxicam in sows with mastitis-metritis-agalactia syndrome". Journal of Veterinary Pharmacology and Therapeutics, vol. 26, 2003, pp. 355-360.
http://dictionary.reference.com/search?q=ambient.
Hydrated Silica Webpage; http://science.kosmix.com/topic/hydrated_silica; Kosmix Corporation, Apr. 21, 2011, pp. 1-14.
International Search Report and Written Opinion for PCT/EP2011/056610 dated Jan. 26, 2012.
Jain et al., "Antiplatelet therapy in acute coronary syndromes without persistent ST-segment elevation". Cardiovascular Drugs and Therapy, vol. 15, No. 5, Sep. 2001, pp. 423-436. [Abstract Only].
Kimura et al., "Effect of cilostazol on platelet agrregation and experimental thrombosis". Arzneimittel-Forschung, vol. 35, No. 7A, 1985, pp. 1144-1149. [Abstract Only].
Kumar et al., "Comparative Studies on Effect of Some Hydrophilic Polymers on the Dissolution Rate of a Poorly Water Soluble Drug, Meloxicam". Indian Drugs, vol. 39, No. 6, Apr. 2002, pp. 323-329.
Lieberman et al., "Tablet Formulation and Design" in Pharmaceutical Dosage Forms: Tablets, vol. 1, Second Edition, Marcel Dekker, Inc., New York, New York, 1989, pp. 105-108.
Luger et al., "Structure and physicochemical properties of meloxicam, a new NSAID". European Journal of Pharmaceutical Sciences, vol. 5, 1996, pp. 175-187.
Macdonald Campus of McGill University, "Mastitis in Dairy Cows", published online, Jul. 2003, pp. 1-12.
McDonald et al., "Calpain inhibitor I reduces the activation of nuclear factor-KappaB and Organ Injury/Dysfunction in Hemorrhagic Shock". The FASEB Journal, vol. 15, Jan. 2001, pp. 171-186.
Noble et al., "Meloxicam". Drugs, vol. 51, No. 3, Mar. 1996, pp. 424-430.
Parikh et al., Binders and Solvents, Chapter 4, Handbook of Pharmaceutical Granulation Technology, First Edition, Marcel Dekker,1997, pp. 59-67.
Physicians' Desk Reference, 55th Edition, Medical Economics Company, Inc., 2001, pp. 981-984 and pp. 1404-1406.

(56) References Cited

OTHER PUBLICATIONS

Rantanen et al., "Process Analysis of Fluidized Bed Granulation". AAPS PharmsciTech, vol. 2, No. 4, Article 21, 2001, 8 pages.
Remington: The Science and Practice of Pharmacy, 19th Edition, vol. II, Mack Publishing Company, Easton, Pennsylvania, 1995, p. 1646.
Robson et al., "Intrinsic acute renal failure (ARF) associated with non-steroidal anti-inflammatory drug (NSAID) use in juvenile cats undergoing routine desexing—16 cases 1998-2005". May 2006, Journal of Veterinary Internal Medicine, vol. 20, No. 3, Abst. 109, p. 740.
Rudnic et al., "Oral Solid Dosage Forms".,Gennaro, Editior, Remington's Pharmaceutical Sciences, 18th Edition, Mack Publishing Company, Easton, PA, 1990, pp. 1633-1645 and pp. 1654-1655.
Saha et al., "Effect of solubilizing excipients on permeation of poorly water-soluble compounds across Caco-2 cell monolayers". European Journal of Pharmaceutics and Biopharmaceutics, vol. 50, No. 3, 2000, pp. 403-411, Abstract accessed at http://cat.inist.fr/?aModele=afficheN&cpsidt=798854, accessed on Aug. 13, 2010, 3 pages.
Schneeweis et al., "In Vivo and In Vitro Diclofenac Sodium Evaluation After Rectal Application of Soft Gelatine Capsules Enabling Application Induced Transformation (AIT) into a Seminsolid System of Liquid Crystals (SSLC) for Controlled Release". Pharmaceutical Research, vol. 14, No. 12, Dec. 1997, pp. 1726-1729.
sciencelab.com, "Lactose, Monohydrate, Spray-Dried Powder, NF". Accessed at http://www.epoxy-paint.net/page/.S/PVAR/10419/SLL1454, Feb. 29, 2008, 2 pages.
Sorbera et al., "Lumiracoxib Antiarthritic, COX-2 Inhibitor". Drugs of the Future, vol. 27, No. 8, Aug. 2002, pp. 740-747.
Stei et al., "Local Tissue Tolerability of Meloxicam, a New NSAID: Indications for Parental, Dermal and Mucosal Administration". British Journal of Rheumatology, vol. 35, Supp. 1, 1996, pp. 44-50.
Straus et al., "New Evidence for Stroke Prevention: Clinical Applications". The Journal of the American Medical Association, vol. 288, No. 11, Sep. 2002, pp. 1396-1398.
Straus et al., "New Evidence for Stroke Prevention: Scientific Review". The Journal of the American Medical Association, vol. 288, No. 11, Sep. 2002, pp. 1388-1395.
Sunose et al., "The Effect of Cyclooxygenase 2 Inhibitor, FK3311, on Ischemia-Reperfusion Injury in Canine Lung Transplantation". Journal of Heart and Lung Transplantation, vol. 19, No. 1, Jan. 2000, p. 40.
Tuerck et al., "Clinical Pharmacokinetics of Meloxicam". Arzneimittel-Forschung, vol. 47, No. 3, 1997, pp. 253-258.
Tunuguntla et al., "Management of Prostatitis". Prostate Cancer and Prostatic Diseases, vol. 5, No. 3, 2002, pp. 172-179.
Vippagunta et al., "Crystalline solids". Advanced Drug Delivery Reviews, vol. 48, 2001, pp. 3-26.
Wagenlehner et al., "Therapy of Prostatitis Syndrome". Der Urologe [A], vol. 40, No. 1, pp. 24-28.
Gunew et al., "Long-term safety, efficacy and palatability of oral meloxicam at 0.01-0.03 mg/kg for treatment of osteoarthritic pain in cats". Journal of Feline Medicine and Surgery, vol. 10, 2008, pp. 235-241.
Abstract in English for JPH06157312, 1994.
Ansel et al., "Dosage Form Design: Pharmaceutic and Formulation Considerations". Pharmaceutical Dosage Forms and Drug Delivery Systems, Seventh Edition, Lippincott Williams & Wilkins, Philadelphia, PA, 1999, pp. 66 and pp. 89.
Nell, et al., "Comparison of vedaprofen and meloxicam in dogs with muskuloskeletal pain and inflammation". Journal of Small Animal Practce, vol. 43, No. 5, May 2002, pp. 208-212 [Accessed at http://ncbi.nlm.nih.gov/pubmed/10238853 on Sep. 27, 2013]. Abstract Only, 1 page.
Abstract in English for IT1251650, 1995.
Abstract in English of ES2065846, 1995.
Abstract in English of JP2001170083, 2001.
Abstract in English of JP3550782, 2004.
Bunji, Kouho, "Tissue Damage Due to Infections". Drug Injection Handbook, Fundamentals of Blending Variation for Injection Drugs, Nanzando Co. Ltd., Tokyo, 1976, p. 5.
Chemical Abstracts, vol. 118, No. 18, Abstract No. 175803, XP002087682, 1993, 1 page.
Gerritsen et al., "Prostaglandin Synthesis and Release from Cultured Human Trabecular-meshwork Cells and Scleral Fibroblasts". Experimental Eye Research, vol. 43, No. 6, 1986, pp. 1089-1102.
Herbort et al., "Anti-inflammatory Effect of Topical Diclofenac After Argon Laser Trabeculoplasty: Preliminary Results of a Placebo Controlled Study". Klin. Monatsbl. Augenheik, vol. 200, No. 5, May 1992, pp. 358-361.
Li et al., "Degradation mechanism and kinetic studies of a novel anticancer agent, AG2034". International Journal of Pharmaceutics, vol. 167, 1998, pp. 49-56.
Masferrer et al., "Cyclooxygenase-2 Inhibitors: A New Approach to the Therapy of Ocular Inflammation". Survey of Ophthalmology, vol. 41, Supp. 2, Feb. 1997, pp. S35-S40.
Nash et al., "A Relationship Between Screen Opening and Mesh Size for Standard Sieves"., Pharmaceutical Development and Technology, vol. 2, No. 2, 1997, pp. 185-186.
Pharma Projects, Dialog File 928, Accession Nr. 0021312, Diclofenac, InSite Vision, 1996, 5 pages.
Pharmaceutical Excipent Encyclopedia, Yakuji Nippo Ltd., Tokyo, 1994, pp. 2-5.
Snyder et al., "Corticosteroid Treatment and Trabecular Meshwork Proteases in Cell and Organ Culture Supernatants". Experimental Eye Research, vol. 57, No. 4, 1993, pp. 461-468.
"Committee for Veterinary Medicinal Products Meloxicam Summary Report (1)". The European Agency for the Evaluation of Medicinal Products, Jun. 1997, pp. 1-7.

\* cited by examiner

_US 9,795,568 B2_

LOW CONCENTRATION MELOXICAM TABLETS

FIELD OF THE INVENTION

The present invention is directed towards a novel oral application form comprising a divisible meloxicam tablet and its production method.

BACKGROUND OF THE INVENTION

Meloxicam (4-hydroxy-2-methyl-N-(5-methyl-2-thiazolyl)-2H-1,2-benzothiazine-3-carboxamide-1,1-dioxide) is a non-steroidal-anti-inflammatory drug NSAID of the oxicam family. These types of drugs inhibit the enzyme prostaglandin H2 synthase, also called cyclooxygenase or COX. Meloxicam has anti-inflammatory, antipyretic and analgesic properties.

Meloxicam and its sodium and meglumine salts are described in EP0002482 (entirely incorporated by reference). The active ingredient alone has a low water solubility as shown in EP0945134 (entirely incorporated by reference) that also discloses the pH dependent solubility of meloxicam and its salts. There are many different application forms of meloxicam including a solution (EP1299107), a suspension (EP1066029), water-soluble granules (EP1558262), tablets made of either granules containing meloxicam (EP1942902) or of directly compressed powder mixtures (EP1385483 and GB2455875), all entirely incorporated by reference.

The objective of the present invention is to develop a readily accepted, chewable solid meloxicam tablet allowing precise dosage administration of meloxicam, even in low concentrations.

DESCRIPTION OF THE INVENTION

Figure 1A:
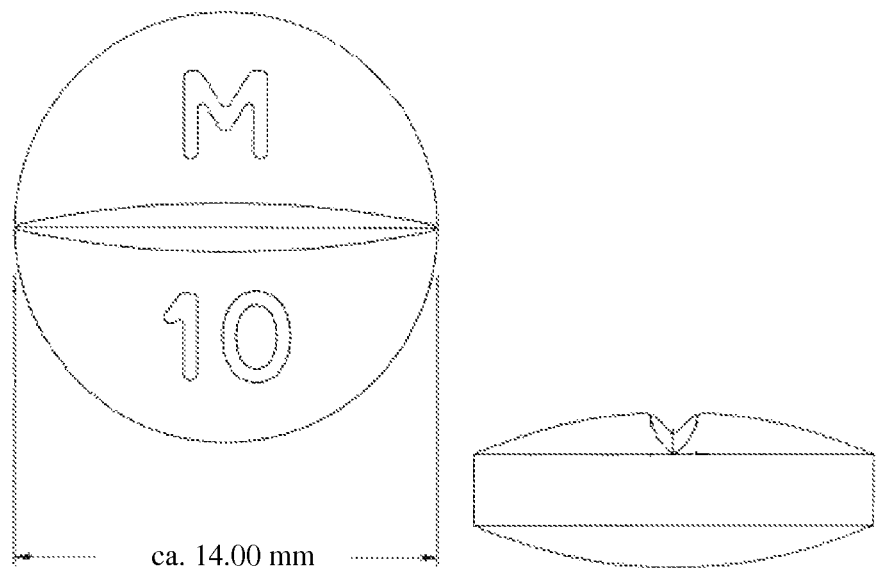
FIG. 1A: Tablet shape and dimensions of 1 mg meloxicam tablets.

Surprisingly, it has been found that such a readily accepted, chewable solid meloxicam tablet allowing precise administration of meloxicam even for exceptionally low concentrations may be prepared by the method of the current invention which is performed by direct compression of powders without any granulation step.

The tablet is administered to companion animals such as feline and canine, preferably canine, with a various body weights, including but not limited to, 1 kg to 70 kg, 1 kg to 60 kg, 1 kg to 50 kg, 1 kg to 40 kg, 1 kg to 30 kg, 1 kg to 20 kg, or 1 kg to 10 kg. The tablet is administered to animals suffering from, for example, inflammation and pain in both acute and chronic musculoskeletal disorders, in order to treat or alleviate such disorders. Other indications include locomoter disorders, lameness, respiratory diseases, and pain such as postoperative pain, fever and inflammation.

The invention relates to a solid tablet that is directly-compressed of powder, comprising meloxicam or a pharmaceutically acceptable salt thereof and one or more excipients, characterized in that the tablets may be broken into two, three or four units with each unit containing equal amounts of the active ingredient. A tablet is characterized in that meloxicam is homogenously dispersed within the tablet. In another embodiment, the invention relates to a solid tablet that is directly-compressed of powder, comprising meloxicam or a pharmaceutically acceptable salt thereof and at least one excipient which is preferably homogenously dispersed within the tablet that may be broken into two, three and/or four units, preferably two or four, more preferably two, with each unit containing equal amounts of the active ingredient. The tablet contains excipients, including but not limited to, fillers/disintegrants, pH adjusters, colorants, flow regulators, lubricants, flavors and mixtures thereof.

At least one of the excipients may be a filler/disintegrant, including but not limited to, starch (such as, but not limited to, maize starch), microcrystalline cellulose, calcium phosphate, lactose, maltodextrin mannitol, sorbitol, cross-linked polyvinyl pyrrolidone, sodium carboxymethyl cellulose, and mixtures thereof, preferably starch and microcrystalline cellulose. When starch is the filler/disintegrant, then the concentration is preferably in the range of 150 mg to 450 mg per tablet, preferably 150 to 300 mg, 160 to 290 mg, 170 to 280 mg, 170 to 270 mg, 180 to 260 mg, 170 to 250 mg, 190 to 240 mg, 200 to 240 mg, 210 to 240 mg, 220 to 240 mg or 230 to 240 mg per tablet, more preferably about 235.0 mg per tablet, which is especially preferred in the tablet containing 1 mg meloxicam.

Another preferred concentration is preferably 200 to 450 mg, 210 to 440 mg, 220 to 430 mg, 230 to 420 mg, 240 to 410 mg, 250 to 400 mg, 260 to 390 mg, 270 to 380 mg, 280 to 370 mg, 290 to 360 mg, 300 to 360 mg, 310 to 360 mg, 320 to 360 mg, 330 to 360 mg, 340 to 360 mg or 350 to 360 mg per tablet, and more preferably about 351.5 mg per tablet, of which about 351.5 mg per tablet is especially preferred in the tablet containing 2.5 mg meloxicam per tablet.

A second filler/disintegrant may be included in the solid tablet or formulation and may have a concentration of preferably 300 to 800 mg per tablet, more preferably 300 to 600 mg, 300 to 500 mg, or 400 to 500 mg per tablet, and most preferably about 400 mg per tablet, which is especially preferred in the tablet containing 1 mg meloxicam. Another preferred concentration is preferably 400 to 800 mg, 500 to 700 mg, 500 to 600 mg per tablet or about 600 mg per tablet, of which about 600 mg per tablet is especially preferred in the tablet containing 2.5 mg meloxicam per tablet.

Coloring agents or colorants may also be used in the present invention. Colorants that are preferably used in the tablet are ferric oxide brown and/or ferric oxide yellow, more preferred is a mixture of ferric oxide brown and ferric oxide yellow. The concentration of each coloring agent is in the range from 2 to 8 mg per tablet, a preferred concentration is in the ranges of 3 to 5 mg per tablet, 3 to 4 mg per tablet or 3.2 mg per tablet, the 3.2 mg amount is especially preferred in the tablet containing 1 mg meloxicam. Another preferred concentration is in the range of 3 to 8 mg per tablet, 4 to 6 mg per tablet, 3 to 5 mg per tablet or 4.8 mg per tablet, which is especially preferred in the tablet containing 2.5 mg meloxicam per tablet.

The tablet may contain a pH adjuster, including but not limited to, tartaric acid, maleic acid, sodium citrate dihydrate, or mixtures thereof, and more preferably sodium citrate dihydrate. The concentration of a pH adjuster is preferably in the range from 50 mg to 150 mg; preferred concentrations of the pH adjuster include 50 to 100 mg, 50 to 90 mg, 50 to 80 mg, 50 to 70 mg, 60 to 90 mg, 60 to 80 mg or 60 to 70 mg per tablet, more preferred is about 65.6 mg per tablet in the tablet containing 1 mg meloxicam. Another preferred concentration is in the range of 75 to 150 mg, 85 to 140 mg, 85 to 130 mg, 85 to 120 mg, 85 to 110 mg, 85 to 100 mg, 90 to 150 mg, 90 to 140 mg, 90 to 130 mg, 90 to 120 mg, 90 to 110 mg, 90 to 100 mg per tablet or about 98.4 mg per tablet, which is especially preferred in the tablet containing 2.5 mg meloxicam per tablet.

The tablet may also contain a flow regulator, which may include, but is not limited to talc, anhydrous silicon dioxide, or mixtures thereof, and preferably anhydrous silicon dioxide. The preferred concentration of a flow regulator is in the range from 2 to 8 mg, preferred concentrations of the flow regulator include 2 to 6 mg, 3 to 6 mg, 3 to 5 mg, 3 to 4 mg, 2 to 5 mg or 2 to 4 mg per tablet and more preferred of about 4 mg, of which about 4 mg is especially preferred in the tablet containing 1 mg meloxicam. Another preferred concentration includes 4 to 8 mg, 5 to 8 mg, 6 to 8 mg, 6 to 7 mg, 5 to 7 mg, 4 to 7 mg, 4 to 6 mg, 5 to 6 mg per tablet, and about 6 mg per tablet, of which about 6 mg per tablet is especially preferred in the tablet containing 2.5 mg meloxicam per tablet.

The tablet may also further contain lubricants including macrogols (polyethylene glycol), stearic acid, aluminium stearate, calcium arachidate (also known as calcium diicoanoate), magnesium stearate, and mixtures thereof; preferably stearic acid, aluminium stearate, calcium arachidate and magnesium stearate; most preferred is magnesium stearate. The concentration range of the lubricant is from about 5 to 15 mg per tablet. Preferred concentrations of the lubricant include, but are not limited to, 5 to 10 mg, 5 to 9 mg, 5 to 8 mg, 6 to 10 mg, 6 to 9, 6 to 8 mg, 7 to 10 mg, 7 to 9 mg, 7 to 8 mg per tablet or 8 mg per tablet, of which the 8 mg per tablet concentration is especially preferred in the tablet containing 1 mg meloxicam.

Another preferred concentration range of the lubricant is selected from the group consisting of 8 to 15 mg, 8 to 14 mg, 8 to 13 mg, 8 to 12 mg, 9 to 15 mg, 9 to 14 mg, 9 to 13 mg, 9 to 12 mg, 10 to 15 mg, 10 to 14 mg, 10 to 13 mg, 10 to 12 mg, 11 to 15 mg, 11 to 14 mg, 11 to 13 mg, 11 to 12 mg per tablet or 12 mg per tablet, of which the 12 mg concentration is especially preferred in the tablet containing 2.5 mg meloxicam per tablet.

Flavoring may also be included in the tablet of the invention. The flavor may be any pharmaceutically or veterinarally acceptable flavor, whether natural or artificial. The flavor is preferably an artificial beef flavor with a concentration range from about 40 to 160 mg per tablet. Preferred concentrations of the flavor include 40 to 100 mg, 50 to 100 mg, 60 to 100 mg, 70 to 100 mg, or 80 to 100 mg per tablet; with about 80 mg per tablet being especially preferred in the tablet containing 1 mg meloxicam.

Other preferred concentration ranges of the flavor are from about 90 to 160 mg, 100 to 150 mg, 110 to 140 mg, 110 to 130 mg per tablet or 120 mg per tablet; with about 120 mg per tablet being especially preferred in the tablet containing 2.5 mg meloxicam per tablet.

According to the invention, the tablet contains 0.5 to 5 mg of meloxicam and has a tablet weight of 500 mg to 2000 mg. Preferably, the tablet contains 0.5 mg to 5 mg of meloxicam and has a total tablet weight of 500 mg to 2000 mg with a tablet diameter ranging from 10 mm to 20 mm. Additionally, the tablet has a height preferably ranging from 3 mm to 8 mm, more preferably 4 mm to 8 mm, 5.3 mm to 7.3 mm or 4.5 mm to 6.5 mm; even more preferred 5 mm, 5.5 mm or 6.3 mm.

The preferred amount of meloxicam per tablet is from 1 mg to 4 mg, more preferred from 1 mg to 3 mg or 1.5 mg to 2.5, even more preferred is 1 mg and 2.5 mg. The tablet has a total weight in the range from 500 to 2000 mg, preferably from 700 to 1500 mg, most preferred 800 mg and 1200 mg. In a preferred embodiment, the tablet containing 0.5 mg to 1.8 mg meloxicam has a total weight of about 500 mg to 900 mg and a diameter ranging from 10 to 15 mm. Even more preferred is a tablet containing 0.5 mg to 1.8 mg meloxicam with a total weight of about 500 mg to 900 mg, a diameter ranging from 10 mm to 15 mm and a height ranging from 4.5 mm to 6.5 mm.

In another preferred embodiment the tablet containing 1.9 to 5 mg meloxicam has a total weight of 900 to 2000 mg and a diameter of 15 mm to 20 mm. Even more preferred is a tablet containing 1.9 to 5 mg meloxicam with a height of 900 mg to 2000 mg, a diameter of 15 mm to 20 mm and a thickness ranging from 5.3 mm to 7.3 mm. In an especially preferred embodiment of the invention, the tablet contains 1 mg meloxicam homogenously dispersed in a total tablet weight of 800 mg or 2.5 mg meloxicam in a tablet with a total weight of 1200 mg.

The flavor contributes 2 to 15% of the total weight of the tablet. According to the invention the tablet most preferably contains 1 mg meloxicam per 800 mg tablet and the flavor content is about 10% by weight per tablet or the tablet contains 2.5 mg meloxicam per tablet with a total weight of 1200 mg with a flavor content of about 10% by weight per tablet.

Figure 1B:
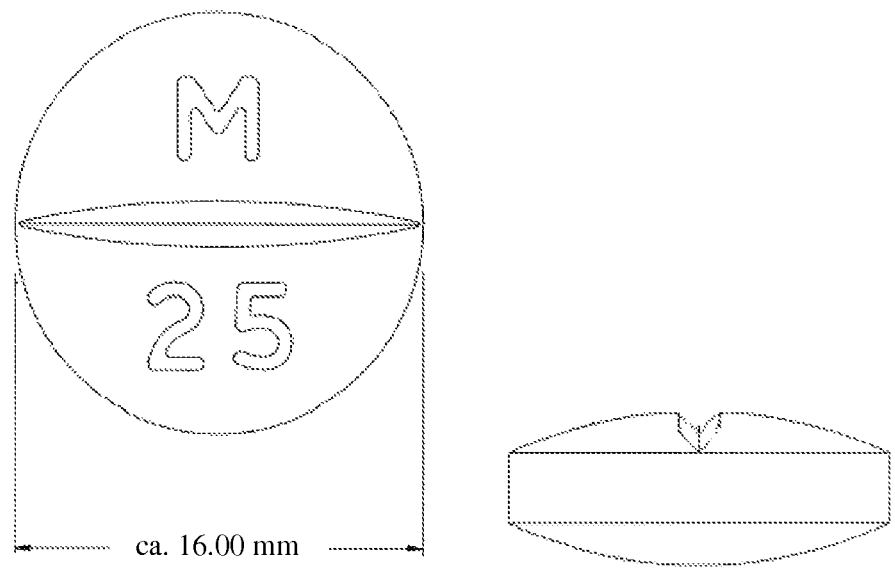
FIG. 1B: Tablet shape and dimensions of 2.5 mg meloxicam tablets.
Figure 2:
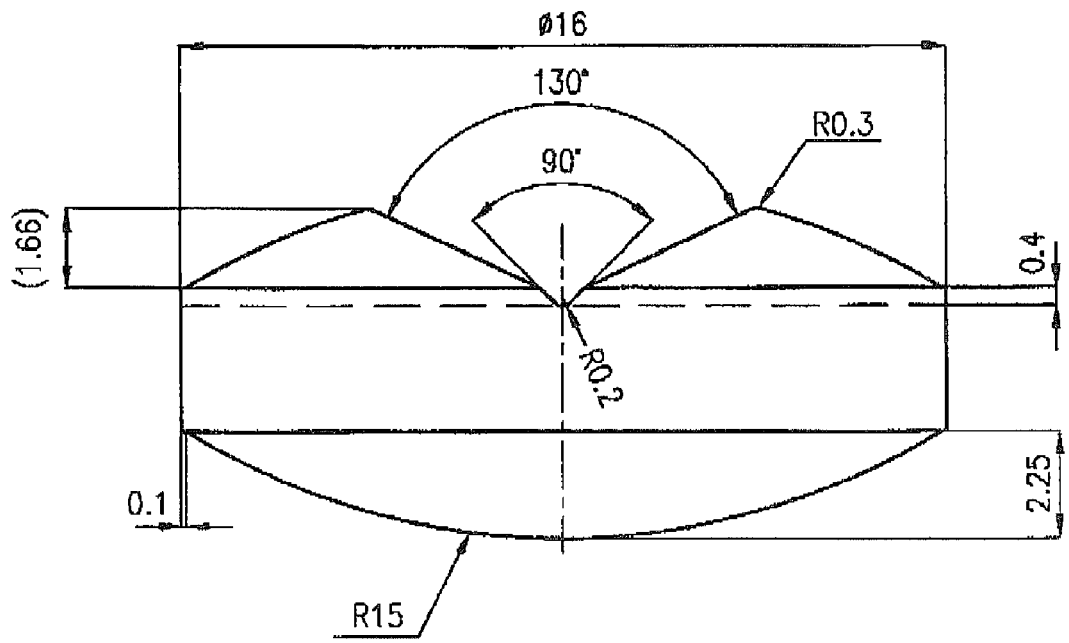
FIG. 2: Tablet shape and breaking notch including dimensions.
Figure 2:
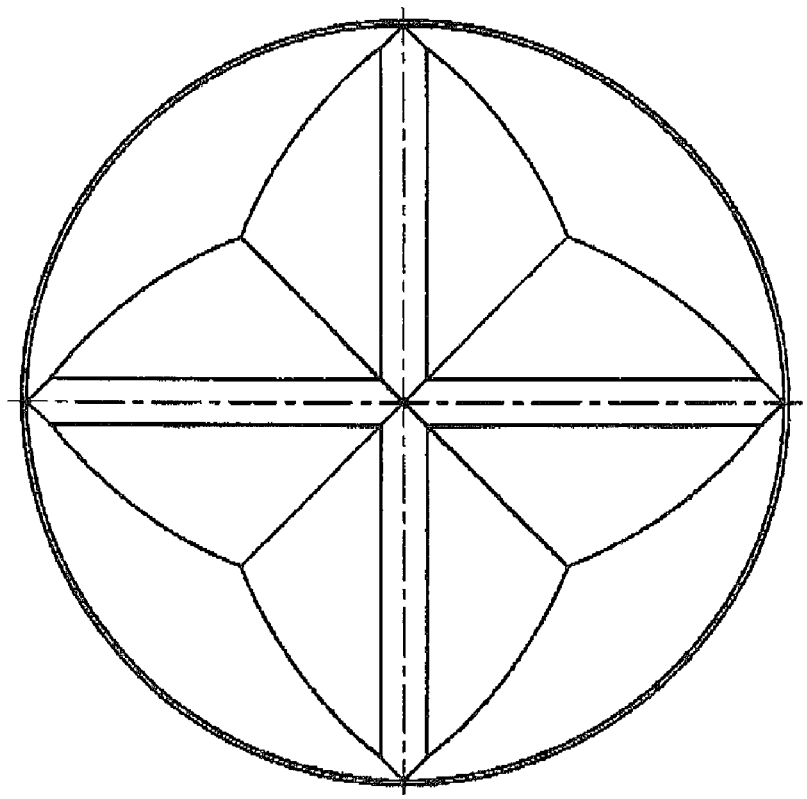

According to another aspect the tablet has a shape as shown, for example in FIGS. 1A, 1B, and FIG. 2. Generally, the tablet contains 0.5 mg to 5 mg of meloxicam and has a total tablet weight of 500 mg to 2000 mg. The dimensions of the tablet are given by its diameter, which ranges from 10 mm to 20 mm, and its height ranging from 3 mm to 8 mm. Preferably the tablet containing 1 mg meloxicam has a total weight of 500 mg to 900 mg, a diameter ranging from 10 mm to 20 mm, 11 mm to 18 mm, 12 mm to 17 mm, 13 mm to 16 mm, or 14 mm to 15 mm.

An alternative preferred range is from 12 mm to 15 mm; and a height ranging from 4 mm to 8 mm, 5 mm to 7 mm, 5 mm to 6 mm, preferably 5 mm to 6 mm. Especially preferred is a tablet, as shown in FIG. 1A, that contains meloxicam in a concentration of 1.0 mg per tablet with a total weight of 800 mg, a diameter of 14 mm and a height of 5.5 mm. Preferably, the tablet containing 2.5 mg meloxicam has a total weight of 900 to 2000 mg, a diameter ranging from 10 mm to 20 mm, 11 mm to 18 mm, 12 mm to 17 mm, 13 mm to 16 mm, or 14 mm to 15 mm.

An alternative preferred range is from 15 mm to 18 mm or 15 mm to 17 mm; and a height ranging from 4 mm to 8 mm, 5 mm to 7 mm, or 5 mm to 6 mm. An alternative preferred range is from 5 mm to 8 mm. Especially preferred is a tablet, as shown in FIG. 1B, containing meloxicam in a concentration of 2.5 mg per tablet with a total weight of 1200 mg, a diameter of 16 mm and a height of 6.3 mm.

As shown in FIGS. 1A and 1B, the tablet has a breaking notch/score line that enables the tablet to be broken into two units resulting in two units containing an equal amount of meloxicam due to its homogenous distribution within the tablet.

According to another aspect of the invention, the tablet has two breaking notches/score lines that are perpendicular to one another as shown in FIG. 2. Thus, the tablet can be quartered resulting into either four or two units of equal amount of meloxicam, which is only possible because of the homogenous distribution of meloxicam in the tablet.

The solid formulation according to the invention is a directly compressed tablet without any granulation step. The active ingredient in the solid formulation is preferably meloxicam as a free base.

In contrast to the state of the art, the tablet according to the invention is produced by compressing a powder directly into a tablet resulting in a low content of the active ingredient meloxicam. Additionally, the tablet has a large size which is desirable as it makes it easier for the animal to pick up the tablet. Additionally, the size was also important to make it easier to divide the tablet in order to achieve a precise administration of the drug, especially in the case of a low dose application. For example, as described above, the tablet containing 1 mg of meloxicam has a diameter of 14 mm, whilst the tablet containing 2.5 mg meloxicam has a diameter of 16 mm.

As previously described, the concentration of the active pharmaceutical ingredient is low and is considered to be in a critical phase. The concentration of meloxicam is in a concentration range that makes it difficult to produce a large tablet with a uniform distribution of the active ingredient within tablet.

Surprisingly, it has been found that the production method of this invention enables a uniform distribution of meloxicam despite the low concentration of the active ingredient. This enables the production of a tablet that can be divided as described with an ensured precise administration. As described above, the tablet of the present invention is preferably marked with a breaking notch/score line that enables the user to break the tablet more easily into two, three or four pieces. The direct compression process comprises the following steps:

1) Mixing meloxicam with 10-50% of a filler/disintegrant, preferably 20 to 40%, more preferred 25-35%, even more preferred is 33%; followed by screening through suitable a mesh that has a mesh size of 0.6 to 1.5 mm, preferably 0.7 to 1.4 mm, more preferred 0.8 to 1.3 mm, even more preferred is a mesh size selected from 0.6 mm, 0.8 mm, 1.0 mm or 1.5 mm.
2) Mixing a pH adjuster and one or more optional coloring agents, followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
3) Mixing of 90-50% of a filler/disintegrant, preferably 60 to 80%, more preferred 60-70%, and even more preferred is about 67%; and optionally a second filler/disintegrant, flow regulator, lubricant and/or artificial flavor may be added, followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
4) Admixing the mixtures or materials obtained in steps 1) and 2) followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
5) Final blending of the mixtures obtained in steps 3) and 4) followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
6) Compression of the powder mixture obtained in step 5) into a tablet.

The direct compression process comprises preferably the following steps:
1) Mixing meloxicam with 10-50% of a filler/disintegrant, preferably 20 to 40%, more preferred 25-35%, even more preferred is 33% of filler/disintegrant, followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
2) Mixing of a pH adjuster and optional colorant, followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
3) Mixing of 90-50% of the filler/disintegrant, preferably 60 to 80%, more preferred 60-70%, even more preferred is 67% of optionally a second filler/disintegrant, lubricant, and flavor, followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
4) Admixing the blends, mixtures or materials obtained in steps 1) and 2) followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm or 1.5 mm.
5) Final blending of the mixture obtained in steps 3) and 4) followed by screening through a suitable mesh that has a mesh size of 0.6 to 1.5 mm, preferably 0.7 to 1.4 mm, more preferred 0.8 to 1.3 mm, even more preferred is a mesh size of 0.6 mm, 0.8 mm, 1.0 mm and 1.5 mm.
6) Compression of the powder mixture obtained in 5) into a tablet.

Thus, a solid tablet comprising meloxicam or a pharmaceutically acceptable salt thereof is provided, where the solid tablet is obtainable by the direct compression process comprising the steps 1 to 6 as described above.

In another embodiment, a solid tablet comprising meloxicam or a pharmaceutically acceptable salt thereof as described herein is provided, where the production of the solid tablet comprises one or more of the process steps 1 to 6 as described above. For example, the production process may comprise step 1, steps 1 and 4, steps 1, 4 and 6 or steps 1, 4, 5 and 6. However, the preferred method comprises steps 1 to 6.

Example: Method of Production

The following description of the production method is just one example and as such should not be understood as limiting.

The first step in the manufacturing process is the premixing of the active ingredient such as meloxicam or a pharmaceutically active salt thereof with a portion of filler/disintegrant such as starch, followed by mesh screening. Due to the low total amount of meloxicam or the pharmaceutically acceptable salt thereof in the tablet mixture, subsequent mixing with, for example about 900 revolutions, is necessary after addition of another screened mixture containing a pH adjuster such as sodium citrate and the option colorants (e.g., ferric oxides) to ensure a homogeneous distribution of the active ingredient in the matrix. Finally, a mixture of screened microcrystalline cellulose, meat flavor, the remaining amount of starch, colloidal silica anhydrous and magnesium stearate is added, followed by a final blending with, for example about 350 revolutions of the mixing container. The final blend is directly compressed into tablets.

Examples

I. Composition for a Tablet with a Total Weight of 800 mg Comprising 1 mg Meloxicam and 10% Flavor

| Ingredients | mg/tablet |
| --- | --- |
| Meloxicam | 1.0 |
| Sodium Citrate Dihydrate | 65.6 |
| Maize Starch | 235.0 |
| Ferric Oxide Brown | 3.2 |
| Ferric Oxide Yellow | 3.2 |
| Microcrystalline Cellulose | 400.0 |
| Artificial Powdered Beef Flavor | 80.0 |
| Anhydrous Silicon Dioxide | 4.0 |
| Magnesium Stearate | 8.0 |
| Total | 800.0 |

II. Composition for a Tablet with a Total Weight of 1200 mg Comprising 2.5 mg Meloxicam and 10% Flavor

| Ingredients | mg/tablet |
| --- | --- |
| Meloxicam | 2.5 |
| Sodium Citrate Dihydrate | 98.4 |
| Maize Starch | 351.5 |
| Ferric Oxide Brown | 4.8 |
| Ferric Oxide Yellow | 4.8 |
| Microcrystalline Cellulose | 600.0 |
| Artificial Powdered Beef Flavor | 120.0 |
| Anhydrous Silicon Dioxide | 6.0 |
| Magnesium Stearate | 12.0 |
| Total | 1200.0 |

The invention claimed is:

1. A solid tablet that is directly-compressed of powder, comprising meloxicam or a pharmaceutically acceptable salt thereof and at least one excipient, wherein meloxicam is homogenously dispersed within the tablet such that the tablet may be broken into two, three or four units with each unit containing equal amounts of said meloxicam or a pharmaceutically acceptable salt, said tablet comprises about 0.5 to 5 mg of meloxicam and has a tablet weight of about 500 mg to 2000 mg, and a weight ratio of meloxicam to tablet is no greater than 0.21%.

2. The tablet according to claim 1, wherein said excipient is selected from the group consisting of fillers/disintegrants, pH adjusters, colorants, flow regulators, lubricants, flavor, and mixtures thereof.

3. The tablet according to claim 2, wherein at least one of the excipients is a filler/disintegrant selected from the group consisting of calcium phosphate, lactose, maltodextrin, mannitol, sorbitol, cross-linked polyvinyl pyrrolidone, sodium carboxymethyl cellulose, starch, microcrystalline cellulose, and mixtures thereof.

4. The tablet according to claim 2, wherein said colorant is ferric oxide brown, ferric oxide yellow or mixtures thereof.

5. The tablet according to claim 2 wherein said pH adjuster is selected from the group consisting of tartaric acid, maleic acid, sodium citrate dihydrate and mixtures thereof.

6. The tablet according to claim 2, wherein said flow regulator is selected from the group consisting of talc, anhydrous silicon dioxide and mixtures thereof.

7. The tablet according to claim 2, wherein said lubricant is selected from the group consisting of polyethylene glycol, stearic acid, aluminum stearate, calcium arachidate, magnesium stearate and mixtures thereof.

8. The tablet according to claim 2, comprising an artificial or natural flavor.

9. The tablet according to claim 8, wherein said flavor is present in an amount of about 2 to 15% by weight of the total tablet weight.

10. The tablet according to claim 8, wherein the flavor is an artificial beef flavor.

11. The tablet according to claim 1, wherein the tablet comprises meloxicam as a free base.

12. The tablet according to claim 1, wherein the powder consists of particles possessing a particle size of 600 μm to 1500 μm.

13. The tablet according to claim 1, wherein the powder consists of particles possessing a particle size of 600 μm to 1000 μm.

14. The tablet according to claim 1, wherein the excipient comprises filler selected from the group consisting of sodium carboxymethyl cellulose.

15. The tablet according to claim 14, wherein the excipient further comprises a pH adjuster selected from the group consisting of tartaric acid, maleic acid, and mixtures thereof.

16. The tablet according to claim 1, wherein the tablet:
contains meloxicam in a concentration of 1 mg per tablet;
possesses a height of from 5 mm to 7 mm;
possesses a diameter of from 11 mm to 18 mm; and
possesses a total weight of 500 mg to 900 mg.

17. The tablet according to claim 1, wherein the tablet:
contains meloxicam in a concentration of 2.5 mg per tablet;
possesses a height of from 5 mm to 8 mm;
possesses a diameter of from 11 mm to 18 mm; and
possesses a total weight of from 900 mg to 2000 mg.

18. The tablet according to claim 1, wherein the powder further comprises particles possessing a particle size of less than 600 μm.

19. A solid tablet that is directly-compressed of powder, comprising meloxicam or a pharmaceutically acceptable salt thereof and at least one excipient, wherein meloxicam is homogenously dispersed within the tablet such that the tablet may be broken into two, three or four units with each unit containing equal amounts of said meloxicam or a pharmaceutically acceptable salt, said tablet comprises about 0.5 to 5 mg of meloxicam and has a tablet weight of about 500 mg to 2000 mg, and the weight ratio of meloxicam to tablet is no greater than 0.125%.

\* \* \* \* \*